United States Patent
Peters et al.

(10) Patent No.: US 7,662,812 B2
(45) Date of Patent: Feb. 16, 2010

(54) DIAZABICYCLIC ARYL DERIVATIVES AND THEIR USE AS CHINOLINERGIC LIGANDS AT NICOTINIC ACETYLCHOLINE RECEPTORS

(75) Inventors: Dan Peters, Malmö (SE); Daniel B Timmermann, Herlev (DK); Gunnar Olsen, Smørum (DK); Elsebet Østergaard Nielsen, København K (DK); Tino Dyhring, Solrød (DK)

(73) Assignee: Neurosearch A/S, Ballerup (DK)

( * ) Notice: Subject to any disclaimer, the term of this patent is extended or adjusted under 35 U.S.C. 154(b) by 23 days.

(21) Appl. No.: 11/884,350

(22) PCT Filed: Feb. 13, 2006

(86) PCT No.: PCT/EP2006/050874

§ 371 (c)(1),
(2), (4) Date: Aug. 15, 2007

(87) PCT Pub. No.: WO2006/087306

PCT Pub. Date: Aug. 24, 2006

(65) Prior Publication Data

US 2008/0146582 A1   Jun. 19, 2008

Related U.S. Application Data

(60) Provisional application No. 60/653,491, filed on Feb. 17, 2005.

(30) Foreign Application Priority Data

Feb. 16, 2005  (DK) ............................... 2005 00230
Dec. 6, 2005   (DK) ............................... 2005 01723

(51) Int. Cl.
*A61K 31/551*  (2006.01)
*A61K 31/501*  (2006.01)
*C07D 487/08*  (2006.01)
*C07D 245/02*  (2006.01)
*C07D 207/325* (2006.01)
*C07D 209/08*  (2006.01)
*C07D 211/60*  (2006.01)
*C07C 69/67*   (2006.01)
*A61P 25/02*   (2006.01)
*A61P 25/30*   (2006.01)

(52) U.S. Cl. .................. 514/221; 514/252.02; 544/238; 544/349; 540/556; 540/460; 540/472; 548/536; 548/470; 546/245; 560/180

(58) Field of Classification Search ............... 514/221; 540/567, 556; 544/235
See application file for complete search history.

(56) References Cited

U.S. PATENT DOCUMENTS

| 5,478,939 A | 12/1995 | Trybulski et al. |
| 2003/0176416 A1 | 9/2003 | Peters et al. |
| 2003/0225268 A1 | 12/2003 | Bunnelle et al. |
| 2005/0101602 A1 | 5/2005 | Basha et al. |
| 2005/0131236 A1 | 6/2005 | Peters et al. |

FOREIGN PATENT DOCUMENTS

| EP | 1 219 622 A2 | 7/2002 |
| WO | WO-98/54181 A1 | 12/1998 |
| WO | WO-98/54182 A1 | 12/1998 |
| WO | WO-99/42465 A2 | 8/1999 |
| WO | WO-00/34279 A1 | 6/2000 |
| WO | WO-00/34284 A1 | 6/2000 |
| WO | WO-00/44755 A1 | 8/2000 |
| WO | WO-00/66586 A1 | 11/2000 |
| WO | WO-01/90109 A1 | 11/2001 |
| WO | WO-01/92259 A1 | 12/2001 |
| WO | WO-01/92260 A1 | 12/2001 |
| WO | WO-01/92261 A1 | 12/2001 |
| WO | WO-02/02564 A1 | 1/2002 |
| WO | WO-02/096911 A1 | 12/2002 |
| WO | WO-03/044019 A1 | 5/2003 |
| WO | WO-03/044020 A1 | 5/2003 |
| WO | WO-03/044024 A1 | 5/2003 |
| WO | WO-03/094831 A2 | 11/2003 |
| WO | WO-2004/029053 A1 | 4/2004 |
| WO | WO-2004/043960 A1 | 5/2004 |
| WO | WO-2005/074940 A1 | 8/2005 |
| WO | WO-2006/045716 A1 | 5/2006 |

OTHER PUBLICATIONS

Maviel, et al., Neuroscience, vol. 120, # 4, Sep. 15, 2003, pp. 1049-1059.*

* cited by examiner

*Primary Examiner*—Mark L. Berch
*Assistant Examiner*—Cecilia M Jaisle
(74) *Attorney, Agent, or Firm*—Birch, Stewart, Kolasch & Birch, LLP.

(57) ABSTRACT

This invention relates to novel diazabicyclic aryl derivatives which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

14 Claims, No Drawings

DIAZABICYCLIC ARYL DERIVATIVES AND THEIR USE AS CHINOLINERGIC LIGANDS AT NICOTINIC ACETYLCHOLINE RECEPTORS

This application is the National Phase of PCT application PCT/EP2006/050874, filed Feb. 13, 2006 and claims priority under 35 U.S.C. 119(e) to U.S. Provisional Application No. 60/653,491 filed on Feb. 17, 2005 and under 35 U.S.C. 119(a) to Patent Application Nos. PA 2005 00230 and PA 2005 01723 filed in Denmark on Feb. 16, 2005 and Dec. 6, 2005, respectively. These prior applications are hereby expressly incorporated by reference into the present application.

TECHNICAL FIELD

This invention relates to novel diazabicyclic aryl derivatives, which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

SUMMARY OF THE INVENTION

The present invention is devoted to the provision novel modulators of the nicotinic and/or of the monoamine receptors, which modulators are useful for the treatment of diseases or disorders related to the cholinergic receptors, and in particular the nicotinic acetylcholine receptor (nAChR), the serotonin receptor (5-HTR), the dopamine receptor (DAR) and the norepinephrine receptor (NER), and of the biogenic amine transporters for serotonin (5-HT), dopamine (DA) and norepinephrine (NE).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel diazabicyclic aryl derivatives represented by Formula I

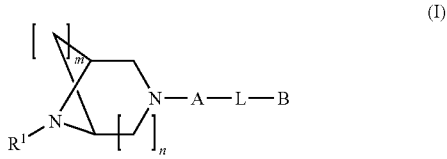

(I)

any of its enantiomers or any mixture of its enantiomers, or a pharmaceutically acceptable salt thereof, wherein m is 2 or 3; and n is 1 or 2; and $R^1$ represents hydrogen, alkyl, cycloalkyl or cycloalkyl-alkyl;

A represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro;

B represents a phenyl or naphthyl group, a 5-6 membered aromatic monocyclic heterocyclic group, or an aromatic bicyclic heterocyclic group; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, —NH(CO)R' and NH(CO)NHR'; wherein R' represents hydrogen, alkyl, cycloalkyl or phenyl; and L represents —O—, —S—, —S—CH$_2$—, —CH$_2$—S—, —SO—, —SO$_2$—, —NR"—, —CH$_2$—, —CH$_2$—CH$_2$—, —CH=CH—, —C≡C—, —NR"CO—, —NR"CONR"— or —NR"(SO$_2$)—; wherein R" represents hydrogen or alkyl.

In its second aspect the invention provides pharmaceutical compositions comprising a therapeutically effective amount of the diazabicyclic aryl derivative of the invention, or a pharmaceutically-acceptable addition salt thereof, or a prodrug thereof, together with at least one pharmaceutically-acceptable carrier or diluent.

In a further aspect the invention relates to the use of the diazabicyclic aryl derivative of the invention, or a pharmaceutically-acceptable addition salt thereof, for the manufacture of a pharmaceutical composition/medicament for the treatment, prevention or alleviation of a disease or a disorder or a condition of a mammal, including a human, which disease, disorder or condition is responsive to modulation of cholinergic receptors and/or monoamine receptors.

In a final aspect the invention provides methods of treatment, prevention or alleviation of diseases, disorders or conditions of a living animal body, including a human, which disorder, disease or condition is responsive to modulation of cholinergic receptors and/or monoamine receptors, which method comprises the step of administering to such a living animal body in need thereof a therapeutically effective amount of the diazabicyclic aryl derivative of the invention.

Other objects of the invention will be apparent to the person skilled in the art from the following detailed description and examples.

DETAILED DISCLOSURE OF THE INVENTION

Diazabicyclic Aryl Derivatives

In a first aspect novel diazabicyclic aryl derivatives are provided. The diazabicyclic aryl derivatives of the invention may be represented by the general Formula I

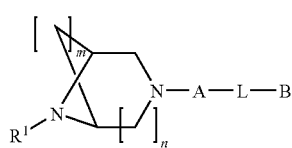

(I)

any of its enantiomers or any mixture of its enantiomers, or a pharmaceutically acceptable salt thereof, wherein m is 2 or 3; and n is 1 or 2; and $R^1$ represents hydrogen, alkyl, cycloalkyl or cycloalkyl-alkyl;

A represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro;

B represents a phenyl or naphthyl group, a 5-6 membered aromatic monocyclic heterocyclic group, or an aromatic bicyclic heterocyclic group; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, —NH(CO)R' and NH(CO)NHR'; wherein R' represents hydrogen, alkyl, cycloalkyl or phenyl; and L represents —O—, —S—, —S—CH$_2$—, —CH$_2$—S—, —SO—, —SO$_2$—, —NR"—, —CH$_2$—, —CH$_2$—CH$_2$—, —CH=CH—, —C≡C—, —NR"CO—, —NR"CONR"— or —NR"(SO$_2$)—; wherein R" represents hydrogen or alkyl.

In a preferred embodiment the diazabicyclic aryl derivative of the invention is a compound of Formula I wherein m is 2 or 3; and n is 1 or 2.

In a more preferred embodiment m is 2; and n is 1 or 2.

In an even more preferred embodiment m is 2; and n is 1.

In a still more preferred embodiment m is 2; and n is 2.

In a yet more preferred embodiment m is 3; and n is 1.

In another preferred embodiment the diazabicyclic aryl derivative of the invention is a compound of Formula I wherein $R^1$ represents hydrogen, alkyl, cycloalkyl or cycloalkyl-alkyl.

In a more preferred embodiment $R^1$ represents hydrogen or alkyl.

In an even more preferred embodiment $R^1$ represents alkyl.

In a still more preferred embodiment $R^1$ represents hydrogen methyl, ethyl or propyl.

In a yet more preferred embodiment $R^1$ represents methyl, ethyl or propyl.

In a yet still more preferred embodiment $R^1$ represents methyl.

In a third preferred embodiment the diazabicyclic aryl derivative of the invention is a compound of Formula I wherein A represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro.

In a more preferred embodiment A represents a phenyl group.

In an even more preferred embodiment A represents a 5-membered aromatic monocyclic heterocyclic group selected from furanyl, thienyl, pyrrolyl, oxazolyl, thiazolyl, imidazolyl, pyrazolyl, isoxazolyl, isothiazolyl, oxadiazolyl, triazolyl and thiadiazolyl.

In a yet more preferred embodiment A represents a 6-membered aromatic monocyclic heterocyclic group selected from pyridinyl, pyridazinyl, pyrimidinyl, pyrazinyl and triazinyl.

In a still more preferred embodiment A represents a pyrid-2,5-diyl group, a pyrid-3,6-diyl group, a pyridazin-3,6-diyl group, a pyrimidin-2,4-diyl group, a pyrimidin-4,6-diyl group, a pyrazin-2,5-diyl group, a pyrazin-2,6-diyl group or a triazin-2,4-diyl group.

In a yet still more preferred embodiment A represents a phenyl, a thiadiazolyl, a pyridinyl or pyridazinyl group.

In a further preferred embodiment A represents a pyridazinyl group, in particular pyridazin-3,6-diyl or pyridazin-3,5-diyl.

In a most preferred embodiment A represents a pyridazin-3,6-diyl group.

In a fourth preferred embodiment the diazabicyclic aryl derivative of the invention is a compound of Formula I wherein B represents a phenyl or naphthyl group, a 5-6 membered aromatic monocyclic heterocyclic group, or an aromatic bicyclic heterocyclic group; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, —NH(CO)R' and NH(CO)NHR'; wherein R' represents hydrogen, alkyl, cycloalkyl or phenyl.

In a more preferred embodiment B represents a phenyl or naphthyl group, a 5-6 membered aromatic monocyclic heterocyclic group, or an aromatic bicyclic heterocyclic group; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl.

In an even more preferred embodiment B represents a phenyl or naphthyl group, a thiadiazolyl group, a pyridinyl group or a pyridazinyl group; which aromatic group may optionally be substituted one or two times with substituents selected from the group consisting of alkyl, cycloalkyl, hydroxy, alkoxy, cyanoalkyl, halo, trihaloalkyl and trihaloalkoxy.

In a fifth preferred embodiment the diazabicyclic aryl derivative of the invention is a compound of Formula I wherein B represents phenyl, thiadiazolyl, pyridinyl, pyridazinyl or indolyl; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, —NH(CO)R' and NH(CO)NHR'; wherein R' represents alkyl, cycloalkyl or phenyl.

In a more preferred embodiment B represents a phenyl, a thiadiazolyl group, a pyridinyl group or a pyridazinyl group; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents alkyl or cycloalkyl.

In an even more preferred embodiment B represents phenyl, optionally be substituted one or two times with substituents selected from the group consisting of alkyl, cycloalkyl, hydroxy, alkoxy, cyanoalkyl, halo, trihaloalkyl and trihaloalkoxy.

In a yet more preferred embodiment B represents a phenyl group; which aromatic group may optionally be substituted with amino or —NH(CO)R'; wherein R' represents alkyl.

In a sixth preferred embodiment the diazabicyclic aryl derivative of the invention is a compound of Formula I wherein B represents an aromatic bicyclic heterocyclic group; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, —NH(CO)R' and NH(CO)NHR'; wherein R' represents alkyl, cycloalkyl or phenyl.

In a more preferred embodiment B represents an aromatic bicyclic heterocyclic group; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl.

In an even more preferred embodiment B represents an indolyl group; optionally substituted one or more times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents alkyl or cycloalkyl.

In a still more preferred embodiment B represents an indolyl group.

In a seventh preferred embodiment the diazabicyclic aryl derivative of the invention is a compound of Formula I wherein m is 2 or 3; n is 1 or 2; A represents a 5-membered aromatic monocyclic heterocyclic group of formula

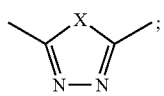

wherein X represents O, S or Se; or a 6-membered aromatic monocyclic heterocyclic group selected from

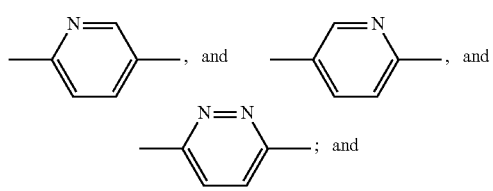

B represents phenyl, naphthyl, thiadiazolyl, pyridinyl, pyridazinyl or indolyl; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, —NH(CO)R' and NH(CO)NHR'; wherein R' represents alkyl, cycloalkyl or phenyl.

In a more preferred embodiment m is 2 or 3; n is 1 or 2; A represents a 5-membered aromatic monocyclic heterocyclic group of formula

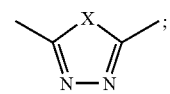

wherein X represents O, S or Se; or a 6-membered aromatic monocyclic heterocyclic group selected from

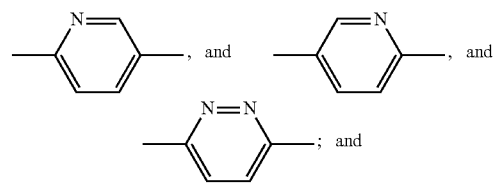

B represents a phenyl or naphthyl group, a thiadiazolyl group, a pyridinyl group or a pyridazinyl group; which aromatic group may optionally be substituted one or two times with substituents selected from the group consisting of alkyl, cycloalkyl, hydroxy, alkoxy, cyanoalkyl, halo, trihaloalkyl, trihaloalkoxy, amino, nitro, and —NH(CO)R'; wherein R' represents alkyl or cycloalkyl.

In an even more preferred embodiment m is 2; n is 1 or 2; A represents a 5-membered aromatic monocyclic heterocyclic group of formula

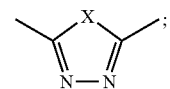

wherein X represents O, S or Se; or a 6-membered aromatic monocyclic heterocyclic group selected from

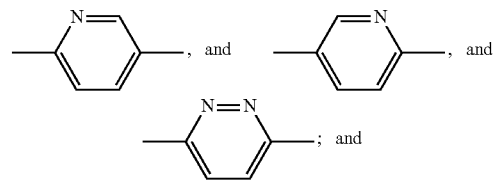

B represents a phenyl or naphthyl group, a thiadiazolyl group, a pyridinyl group or a pyridazinyl group; which aromatic group may optionally be substituted one or two times with substituents selected from the group consisting of alkyl, cycloalkyl, hydroxy, alkoxy, cyanoalkyl, halo, trihaloalkyl and trihaloalkoxy.

In a still more preferred embodiment m is 2; n is 1 or 2; A represents a 6-membered aromatic monocyclic heterocyclic group selected from

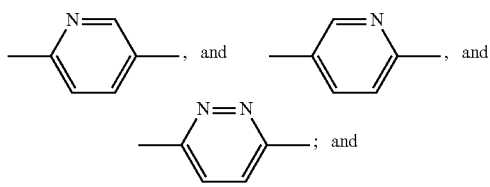

B represents a phenyl group, a thiadiazolyl group, a pyridinyl group or a pyridazinyl group; which aromatic group may optionally be substituted with amino or —NH(CO)R'; wherein R' represents alkyl or cycloalkyl.

In a yet more preferred embodiment m is 2; n is 1 or 2; A represents a 6-membered aromatic monocyclic heterocyclic group selected from

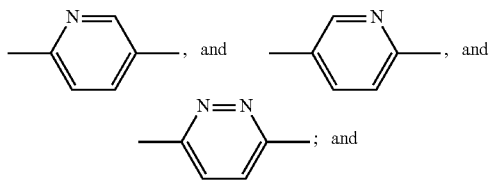

B represents a phenyl group, optionally substituted with amino or —NH(CO)R'; wherein R' represents alkyl.

In a further more preferred embodiment m is 2; n is 1 or 2; A represents

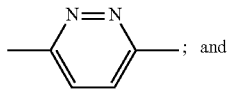

B represents a phenyl group, optionally substituted with amino or —NH(CO)R'; wherein R' represents alkyl.

In an eight preferred embodiment the diazabicyclic aryl derivative of the invention is a compound of Formula I wherein L represents —O—, —S—, —S—CH$_2$—, —CH$_2$—S—, —SO—, —SO$_2$—, —NR"—, —CH$_2$—, —CH$_2$—CH$_2$—, —CH═CH—, —C≡C—, —NR"CO—, —NR"CONR"— or —NR"(SO$_2$)—; wherein R" represents hydrogen or alkyl.

In a more preferred embodiment L represents —O—, —S—, —S—CH$_2$—, —SO—, —C≡C—, —NHCO—, —NHCONH— or —NH(SO$_2$)—.

In a most preferred embodiment L represents —C≡C—.

In a ninth preferred embodiment the diazabicyclic aryl derivative of the invention is a compound of Formula I wherein n is 1 or 2; A represents phenyl, thiadiazolyl, pyridinyl or pyridazinyl; B represents a phenyl, pyridinyl or indolyl, optionally substituted with substituents selected from the group consisting of alkyl, cycloalkyl, hydroxy, alkoxy, cyanoalkyl, halo, trihaloalkyl, trihaloalkoxy, cyano, amino, nitro, —NH(CO)R' and NH(CO)NHR'; wherein R' represents alkyl, cycloalkyl or phenyl; and L represents —O—, —S—, —S—CH$_2$—, —SO—, —C≡C—, —NHCO—, —NHCONH— or —NH(SO$_2$)—.

In a more preferred embodiment m is 2; n is 1 or 2; A represents phenyl, thiadiazolyl, pyridinyl or pyridazinyl; B represents a phenyl or pyridinyl group, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl; and L represents —O—, —S—, —S—CH$_2$—, —SO—, —C≡C—, —NHCO—, —NHCONH— or —NH(SO$_2$)—.

In an even more preferred embodiment m is 2; n is 1 or 2; A represents pyridazinyl; B represents a phenyl, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl; and L represents —O—, —S—, —S—CH$_2$—, —SO—, —C≡C—, —NHCO—, —NHCONH— or —NH(SO$_2$)—.

In a tenth preferred embodiment the diazabicyclic aryl derivative of the invention is a compound of Formula I wherein m is 2 or 3; n is 1 or 2; A represents a 5-membered aromatic monocyclic heterocyclic group of formula

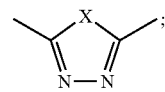

wherein X represents O, S or Se; or
a 6-membered aromatic monocyclic heterocyclic group selected from

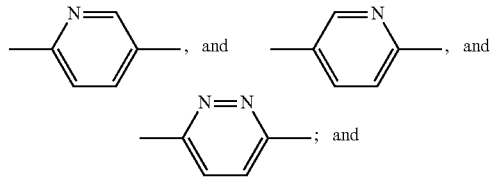

B represents a phenyl, naphthyl, thiadiazolyl, pyridinyl, pyridazinyl or indolyl; which aromatic group may optionally be substituted one or two times with substituents selected from the group consisting of alkyl, cycloalkyl, hydroxy, alkoxy, cyanoalkyl, halo, trihaloalkyl, trihaloalkoxy, amino, nitro, —NH(CO)R' and NH(CO)NHR'; wherein R' represents alkyl, cycloalkyl or phenyl.

In a more preferred embodiment m is 3; n is 1 or 2; A represents a 5-membered aromatic monocyclic heterocyclic group of formula

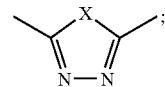

wherein X represents O, S or Se;
or a 6-membered aromatic monocyclic heterocyclic group selected from

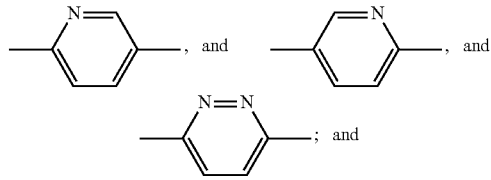

B represents a phenyl or naphthyl group, a thiadiazolyl group, a pyridinyl group or a pyridazinyl group; which aromatic group may optionally be substituted one or two times with substituents selected from the group consisting of alkyl, cycloalkyl, hydroxy, alkoxy, cyanoalkyl, halo, trihaloalkyl, trihaloalkoxy, amino, nitro, and —NH(CO)R'; wherein R' represents alkyl or cycloalkyl.

In an even more preferred embodiment m is 3; n is 1; A represents a 6-membered aromatic monocyclic heterocyclic group selected from

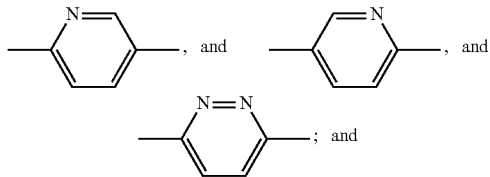

B represents a phenyl group, a thiadiazolyl group, a pyridinyl group or a pyridazinyl group; which aromatic group may optionally be substituted one or two times with substituents selected from the group consisting of alkyl, cycloalkyl, hydroxy, alkoxy, cyanoalkyl, halo, trihaloalkyl, trihaloalkoxy, amino, nitro, and —NH(CO)R'; wherein R' represents alkyl or cycloalkyl.

In a still more preferred embodiment m is 3; n is 1; A represents a 6-membered aromatic monocyclic heterocyclic group selected from

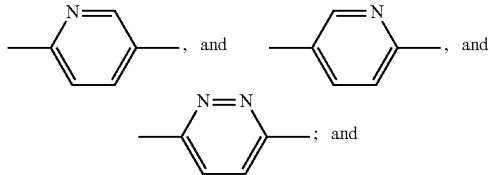

B represents a phenyl group, optionally substituted with amino or —NH(CO)R'; wherein R' represents alkyl.

In a yet more preferred embodiment m is 3; n is 1; A represents

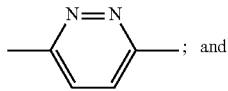

B represents a phenyl group, optionally substituted with amino or —NH(CO)R'; wherein R' represents alkyl.

In its most preferred embodiment the diazabicyclic aryl derivative of the invention is 8-Methyl-3-(6-phenylethynyl-pyridazin-3-yl)-3,8-diaza-bicyclo[3.2.1]octane;

(±)-9-Methyl-3-(6-phenylethynyl-pyridazin-3-yl)-3,9-diaza-bicyclo[4.2.1]nonane;

N-{4-[6-(9-Methyl-9-aza-bicyclo[3.3.1]non-3-yl)-pyridazin-3-ylethynyl]-phenyl}-acetamide;

9-Methyl-3-(6-phenylethynyl-pyridazin-3-yl)-9-aza-bicyclo[3.3.1]nonane;

4-[4-(9-Methyl-3,9-diaza-bicyclo[3.3.1]non-3-yl)-phenylethynyl]-phenylamine;

3-[4-(1H-Indol-5-ylethynyl)-phenyl]-9-methyl-3,9-diaza-bicyclo[3.3.1]nonane;

N-{4-[6-(8-Methyl-3,8-diaza-bicyclo[3.2.1]oct-3-yl)-pyridazin-3-ylethynyl]-phenyl}-acetamide;

4-[6-(8-Methyl-3,8-diaza-bicyclo[3.2.1]oct-3-yl)-pyridazin-3-ylethynyl]-phenylamine;

N-{4-[6-(8-Methyl-3,8-diaza-bicyclo[3.2.1]oct-3-yl)-pyridazin-3-ylethynyl]-phenyl}-benzamide;

N-{4-[6-(8-Methyl-3,8-diaza-bicyclo[3.2.1]oct-3-yl)-pyridazin-3-ylethynyl]-phenyl}propionamide;

N-{4-[6-(8-Methyl-3,8-diaza-bicyclo[3.2.1]oct-3-yl)-pyridazin-3-ylethynyl]-phenyl}-isobutyramide;

3-[6-(1H-Indol-5-ylethynyl)-pyridazin-3-yl]-8-methyl-3,8-diaza-bicyclo[3.2.1]octane;

1-Ethyl-3-{4-[6-(8-methyl-3,8-diaza-bicyclo[3.2.1]oct-3-yl)-pyridazin-3-ylethynyl]-phenyl}-urea; or 8,8-Dimethyl-3-(6-phenylethynyl-pyridazin-3-yl)-3,8-diaza-bicyclo[3.2.1]octane onium iodide salt;

or an enantiomers or a mixture of its enantiomers, or a pharmaceutically acceptable salt thereof.

Any combination of two or more of the embodiments described herein is considered within the scope of the present invention.

Definition of Substituents

In the context of this invention halo represents a fluorine, a chlorine, a bromine or an iodine atom. Thus, a trihalomethyl group represents e.g. a trifluoromethyl group, a trichloromethyl group and similar trihalo-substituted methyl groups.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above. Examples of preferred alkoxy groups of the invention include methoxy and ethoxy.

In the context of this invention a cyanoalkyl group designates an "-alkyl-CN" group, wherein alkyl is as defined above.

In the context of this invention an aromatic monocyclic or bicyclic carbocyclic group designates a monocyclic or polycyclic aromatic hydrocarbon group. Examples of preferred aryl groups of the invention include phenyl, indenyl, naphthyl, azulenyl, fluorenyl, and anthracenyl.

In the context of this invention a 5-6 membered aromatic monocyclic heterocyclic designates a 5-6 membered heteroaryl, which holds one or more heteroatoms in its ring structure. Preferred heteroatoms include nitrogen (N), oxygen (O), and sulphur (S).

Preferred 5-6 membered heteroaryl groups of the invention include furanyl, thienyl, selenophenyl, pyrrolyl (azolyl), oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, and triazinyl.

More preferred 5 membered heteroaryl groups of the invention include furanyl, thienyl, pyrrolyl (azolyl), oxazolyl, thiazolyl, isoxazolyl, isothiazolyl, and thiadiazolyl.

Most preferred 5 membered heteroaryl groups of the invention include furanyl, thienyl, pyrrolyl, oxazolyl, thiazolyl, imidazolyl, pyrazolyl, isoxazolyl, isothiazolyl, oxadiazolyl, triazolyl and thiadiazolyl.

More preferred 6 membered heteroaryl groups of the invention include pyridinyl, pyridazinyl, pyrimidinyl, pyrazinyl and triazinyl.

In the context of this invention an aromatic bicyclic heterocyclic group designates a bicyclic heterocyclic group, which holds one or more heteroatoms in its ring structure. In the context of this invention the term "bicyclic heterocyclic group" includes benzo-fused five- and six-membered heterocyclic rings containing one or more heteroatoms. Preferred heteroatoms include nitrogen (N), oxygen (O), and sulphur (S).

Preferred bicyclic heteroaryl groups of the invention include indolizinyl, indolyl, isoindolyl, benzo[b]furanyl, benzo[b]thienyl, benzoimidazolyl, benzothiazolyl, quinolinyl and isoquinolinyl.

More preferred bicyclic heteroaryl groups of the invention include indolyl, benzo[b]furanyl, benzo[b]thienyl, benzoimidazolyl and benzothiazolyl.

Most preferred bicyclic heteroaryl groups of the invention include indolyl, benzo[b]furanyl, benzo[b]thienyl, and benzothiazolyl.

Pharmaceutically Acceptable Salts

The diazabicyclic aryl derivative of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *Enantiomers, Racemates, and Resolutions*", John Wiley and Sons, New York (1981).

Optical active compounds can also be prepared from optical active starting materials.

Methods of Producing Diazabicyclic Aryl Derivatives

The diazabicyclic aryl derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention is devoted to the provision novel ligands and modulators of the nicotinic receptors, which ligands and modulators are useful for the treatment of diseases or disorders related to the cholinergic receptors, and in particular the nicotinic acetylcholine receptor (nAChR). Preferred compounds of the invention show a pronounced nicotinic acetylcholine α7 receptor subtype selectivity.

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the present invention may be useful for the treatment, prevention or alleviation of a cognitive disorder, learning deficit, memory deficits and dysfunction, Alzheimer's disease, attention deficit, attention deficit hyperactivity disorder (ADHD), Tourette's syndrome, psychosis, depression, Bipolar Disorder, mania, manic depression, schizophrenia, cognitive or attention deficits related to schizophrenia, obsessive compulsive disorders (OCD), panic disorders, eating disorders such as anorexia nervosa, bulimia and obesity, narcolepsy, nociception, AIDS-dementia, senile dementia, autism, Parkinson's disease, Huntington's disease, Amyotrophic Lateral Sclerosis, anxiety, non-OCD anxiety disorders, convulsive disorders, epilepsy, neurodegenerative disorders, transient anoxia, induced neuro-degeneration, neuropathy, diabetic neuropathy, periferic dyslexia, tardive dyskinesia, hyperkinesia, mild, pain, moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, jet-lag, arrhythmias, smooth muscle contractions, angina pectoris, premature labour, diarrhoea, asthma, tardive dyskinesia, hyperkinesia, premature ejaculation, erectile difficulty, hypertension, inflammatory disorders, inflammatory skin disorders, acne, rosacea, Chron's disease, inflammatory bowel disease, ulcerative colitis, diarrhoea, or withdrawal symptoms caused by termination of use of addictive substances, including nicotine containing products such as tobacco, opioids such as heroin, cocaine and morphine, benzodiazepines and benzodiazepine-like drugs, and alcohol.

In a more preferred embodiment the compounds of the invention may be useful for the treatment, prevention or alleviation of pain, mild or moderate or even severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury.

In an even more preferred embodiment the compounds of the invention may be useful for the treatment, prevention or alleviation of diseases, disorders or conditions associated with smooth muscle contractions, convulsive disorders, angina pectoris, premature labour, convulsions, diarrhoea, asthma, epilepsy, tardive dyskinesia, hyperkinesia, premature ejaculation, or erectile difficulty.

In a still more preferred embodiment the compounds of the invention may be useful for the treatment, prevention or alleviation of a neurodegenerative disorder, transient anoxia, or induced neuro-degeneration.

In a yet more preferred embodiment the compounds of the invention may be useful for the treatment, prevention or alleviation of an inflammatory disorder, inflammatory skin disorder, acne, rosacea, Chron's disease, inflammatory bowel disease, ulcerative colitis, or diarrhoea.

In a further preferred embodiment the compounds of the invention may be useful for the treatment, prevention or alleviation of diabetic neuropathy, schizophrenia, cognitive or attentional deficits related to schizophrenia, or depression.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines, benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 µM.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Pharmaceutical Compositions

In another aspect the invention provides novel pharmaceutical compositions comprising a therapeutically effective amount of diazabicyclic aryl derivative of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the diazabicyclic aryl derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The diazabicyclic aryl derivatives of the present invention are valuable nicotinic and monoamine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors and/or monoamine receptors, and which method comprises administering to such a living animal body, including a human, in need thereof an effective amount of an diazabicyclic aryl derivative of the invention.

In a preferred embodiment, the disease, disorder or condition relates to the central nervous system.

In a preferred embodiment, the disease, disorder or condition is anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In a another preferred embodiment, the disease, disorder or condition are associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In a third preferred embodiment, the disease, disorder or condition is related to the endocrine system, such as thyrotoxicosis, pheochromocytoma, hypertension and arrhythmias.

In a fourth preferred embodiment, the disease, disorder or condition is a neurodegenerative disorders, including transient anoxia and induced neuro-degeneration.

In a fifth preferred embodiment, the disease, disorder or condition is an inflammatory disorder, including inflammatory skin disorders such as acne and rosacea, Chron's disease, inflammatory bowel disease, ulcerative colitis, and diarrhoea.

In a sixth preferred embodiment, the disease, disorder or condition is mild, moderate or even severe pain of acute, chronic or recurrent character, as well as pain caused by migraine, postoperative pain, and phantom limb pain.

In a seventh preferred embodiment, the disease, disorder or condition is associated withdrawal symptoms caused by termination of use of addictive substances, including nicotine containing products such as tobacco, opioids such as heroin, cocaine and morphine, benzodiazepines and benzodiazepine-like drugs, and alcohol.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents. Magnesium sulphate was used as drying agent in the workup-procedures and solvents were evaporated under reduced pressure.

Diethyl cis-1-methylpyrrolidine-2,5-dicarboxylate
(Intermediate compound)

Diethyl mezo-2,5-dibromoadipate (101.7 g; 0.283 mol) was dissolved by heating under argon in THF (400 ml) and then cooled to 0° C. To the obtained solution a pre-cooled solution of methylamine (27.3 g; 0.88 mol) in THF (150 ml) was added and the mixture was stirred at room temperature for 18 hours. The separated crystalline material was filtered off, the filtrate concentrated and the residue chromatographed on a silica gel column (10 cm long) with hexane-ethyl acetate 4:1 as eluent to afford 58.9 g (91%).

$^1$H NMR (300 MHz, CDCl$_3$): δ 1.15 (t, 6H); 1.9-2.0 (m, 4H); 2.38 (s, 3H); 2.99 (m, 2H); 4.07 (q, 4H). $^{13}$C NMR (75 MHz, CDCl$_3$): δ 13.98; 27.68; 40.82; 60.39; 67.93; 68.06; 172.32.

3-Benzyl-8-methyl-3,8-diazabicyclo[3.2.1]octane-2,
4-dione (Intermediate compound)

To a solution of diethyl cis-1-methylpyrrolidine-2,5-dicarboxylate (74.8 g; 0.383 mol) in xylene (150 ml) benzylamine (41.0 g; 0.383 mol) was added and the mixture heated to reflux for 16 hours. Then xylene was removed at reduced pressure and the residue was heated at 220° C. for 18 hours. The obtained crude product was distilled by portions (30-40 g) on Büchi oven for distillation at 180° C. and 0.1 mbar, and the first fraction collected (after about 1 hours). The combined first fractions were crystallized from a mixture of hexane and ethyl acetate 1:1 to yield 30.6 (34%).

$^1$H NMR (300 MHz, CDCl$_3$): δ 1.88 (m, 2H); 2.34 (m, 2H); 2.42 (s, 3H); 3.80 (dd, 2H); 4.88 (s, 2H); 7.2-7.4 (m, 5H). $^{13}$C NMR (75 MHz, CDCl$_3$): 26.69; 35.82; 41.26; 65.72; 127.42; 128.36; 128.62; 136.91; 173.26.

3-Benzyl-methyl-3,8-diazabicyclo[3.2.1]octane
(Intermediate compound)

To a solution of 3-benzyl-8-methyl-3,8-diazabicyclo[3.2.1]octane-2,4-dione (28.3 g; 0.116 mol) in 200 ml of absolute dioxane LiAlH$_4$ (7.6 g; 0.2 mol) was added and the mixture boiled under argon for 18 hours. Then a mixture of water (7.5 ml) and dioxane (40 ml) was added drop-wise to the reaction mixture. The suspension was mixed for 20 minutes and filtered trough a dense glass filter. The filtrate was evaporated and the residue was distilled on Büchi oven for distillation at 120° C. and 0.1 mbar. Yield 17.6 g (70%).

$^1$H NMR (300 MHz, CDCl$_3$): δ 1.7-1.9 (m, 4H); 2.18 (s, 3H); 2.25 (d, 2H); 2.48 (dd, 2H); 2.95 (m, 2H); 3.39 (s, 2H); 7.1-7.3 (m, 5H).

8-Methyl-3,8-diazabicyclo[3.2.1]octane
(Intermediate compound)

To a degassed by argon solution of 3-benzyl-8-methyl-3, 8-diazabicyclo[3.2.1]octane (17.6 g; 0.08 mol) in methanol (50 ml), 10% Pd/C (1.0 g) was added and hydrogen passed into reaction mixture for 24 hours. The catalyst was filtered off, the filtrate evaporated and the residue distilled on Büchi oven for distillation at 100° C. and 0.1 mbar. Yield 8.5 g (85%).

$^1$H NMR (300 MHz, CDCl$_3$): δ 1.6 (m, 2H); 1.86 (s, 1H); 1.9-2.0 (m, 2H); 2.17 (s, 3H); 2.53 (m, 2H); 2.9-3.0 (m, 4H). $^{13}$C NMR (75 MHz, CDCl$_3$): δ 24.73; 41.72; 52.10; 62.08.

Method A 3-(6-Bromo-pyridazin-3-yl)-8-methyl-3,8-diazabicyclo[3.2.1]octane fumaric acid salt
(Intermediate compound)

A mixture of 8-methyl-3,8-diazabicyclo[3.2.1]octane (2.0 g; 15.85 mmol), 3,6-dibromopyridazine (3.77 g; 15.85 mmol) and dioxane (20 ml) was stirred at room temperature for 15 hours. Aqueous sodium hydroxide (1 M; 20 ml) was added and the mixture was extracted twice with dichloromethane (2×20 ml). Chromatography on silica gel with dichloromethane, 10% methanol and 1% aqueous ammonia as solvent gave the compound as free base. Yield 1.83 g (41%). The corresponding salt was obtained by addition of a diethyl ether and methanol mixture (9:1) saturated with fumaric acid. Mp. 118.5-119.5° C.

(±)-3-(6-Bromo-pyridazin-3-yl)-9-methyl-3,9-diazabicyclo[4.2.1]nonane fumaric acid salt
(Intermediate compound)

Was prepared according to Method A from (+)-9-methyl-3,9-diazabicyclo-[4.2.1]-nonane. (±)-9-Methyl-3,9-diazabicyclo-[4.2.1]-nonane was prepared according to [Michaels R J and Zaugg H E; J. Org. Chem. 1960 25 637]. Mp. 175.6° C.

Method B

8-Methyl-3-(6-phenylethynyl-pyridazin-3-yl)-3,8-diaza-bicyclo[3.2.1]octane fumaric acid salt
(Compound B1)

A mixture of 3-(6-bromo-pyridazin-3-yl)-8-methyl-3,8-diaza-bicyclo-[3.2.1]octane (1.63 g; 5.76 mmol), phenylacetylene (2.94 g; 28.8 mmol), palladacycle (109 mg; 0.115 mmol), CuI (1.09 g; 5.75 mmol), KI (955 mg; 5.76 mmol), diisopropylethylamine (1.49 g; 11.5 mmol), diehylamine (842 mg; 11.5 mmol) and dioxane (40 ml) was stirred at reflux for 15 hours. Aqueous sodium hydroxide (1 M; 20 ml) was added and the mixture was extracted twice with dichloromethane (2×20 ml). Chromatography on silica gel with dichloromethane, 10% methanol and 1% aqueous ammonia as solvent gave the compound as free base. Yield 1.2 g (68%). The corresponding salt was obtained by addition of a diethyl ether and methanol mixture (9:1) saturated with fumaric acid. Mp. 142.4° C.

N-{4-[6-(8-Methyl-3,8-diaza-bicyclo[3.2.1]oct-3-yl)-pyridazin-3-ylethynyl]-phenyl}acetamide
(Compound B2)

Was prepared according to Method B from 3-(6-bromo-pyridazin-3-yl)-8-methyl-3,8-diaza-bicyclo[3.2.1]octane and N-(4-ethynyl-phenyl)-acetamide. Mp 292° C.

3-[6-(1H-Indol-5-ylethynyl)-pyridazin-3-yl]-8-methyl-3,8-diaza-bicyclo[3.2.1]octane fumaric acid salt
(Compound B3)

Was prepared according to Method B from 3-(6-bromo-pyridazin-3-yl)-8-methyl-3,8-diaza-bicyclo[3.2.1]octane and 5-ethynyl-1H-indole. Mp. 159° C. LC-ESI-HRMS of [M+H]+ shows 344.189 Da. Calc. 344.18752 Da, dev. 4.3 ppm.

(±)-9-Methyl-3-(6-phenylethynyl-pyridazin-3-yl)-3, 9-diaza-bicyclo[4.2.1]nonane fumaric acid salt
(Compound B4)

Was prepared according to Method B from (+)-3-(6-bromo-pyridazin-3-yl)-9-methyl-3,9-diaza-bicyclo[4.2.1] nonane. Mp. 121.3-122.2° C.

Diethyl meso-2,6-dibromopimeloate
(Intermediate compound 1)

Pimelic acid (240 g, 1.5 mol) was placed into a two-necked round bottom flask (1000 ml) fitted with a reflux condenser and an argon inlet. The reflux condenser was connected with two consecutive flasks (500 and 1000 ml). The first flask (500 ml) was placed in to dry ice-isopropanol vessel and the second was half filled with water for HCl absorption. Thionyl chloride (368 g, 3.09 mol) was added in three portions (180, 100 and 88 g) and stirred at 40° C. until gas elution ceased. Finally temperature was raised to 100° C., the first flask with liquid SO$_2$ was disconnected. The flask was fitted with dropping funnel and gas outlet. During 3 hours the flask was continuously irradiated with 300 W UV lamp and bromine (490 g, 3.06 mol) was added dropwise. The HBr formed was absorbed in two consecutive water filled flasks (2×1000 ml). When HBr elution ceased, the dropping funnel was filled with absolute ethanol (200 ml) and carefully added dropwise. The chilled solution was washed with water, aqueous sodium acetate and sodium thiosulfate. The separated organic phase was dried over sodium sulfate, filtrated and distilled in multiple portions (about 40 ml each) by a Büchi oven in vacuo (0.5-1.0 mbar) at 150° C. collecting the fraction from the third flask. Yield: 487 g (87%).

Diethyl cis-1-Methylpiperidine-2,6-dicarboxylate
(Intermediate compound 2)

Diethyl meso-2,6-dibromoadipoate (1) (236 g, 0.631 mol) was placed into a two necked round bottom flask (2000 ml) fitted with a reflux condenser and a thermometer, and was dissolved in absolute THF (400 ml) under argon. A solution of methylamine (62 g, 2.0 mol) in absolute THF (400 ml) was added to the solution of compound 1. The flask was placed in cold water, to prevent it from warming. The reaction mixture was stirred for 18 hours under argon, the separated N-methylammonium bromide was removed by filtration and washed thoroughly with THF. The filtrate was concentrated on a rotary evaporator under reduced pressure and the residue (156 g) was distilled in four portions (about 39 g each) by a Büchi oven in vacuo (0.1-0.4 mbar) at 125° C. (average distillation time 1 hour) collecting the fraction from the third flask. Yield of compound 2 127.5 g (83%) as a light-yellowish oil.

3-Benzyl-9-methyl-3,9-diazabicyclo[3.3.1]nonane-2,
4-dione (Intermediate compound 3)

A solution of diethyl cis-1-methylpiperidin-2,6-carboxylate (127.5 g, 0.524 mol) and benzylamine (57.8 g, 0.540 mol) in xylene (150 ml) was refluxed in a round-bottomed flask (250 ml) for 44 hours. The latter was equipped with a vertical air condenser (15 cm) followed by a Liebig condenser, allowing removal of ethanol from the reaction mixture. The xylene was removed under reduced pressure through a Liebig condenser, the oil bath temperature was elevated to 205° C. and the mixture was heated under argon for 20 hours. The obtained product was distilled in four portions (about 45 g each) by a Büchi oven in vacuo (0.1 mbar) at 160° C. (average distillation time 1 hour) collecting the fraction from the third flask. The three combined 3$^{rd}$ fractions (96 g) were dissolved by boiling in 50 ml of ethyl acetate and allowed to crystallize at room temperature for 3 days. The crystalline material was filtered off, washed with a small amount of ethyl acetate and dried in vacuo to afford 39.5 g of the product as a white crystalline solid. The filtrate was concentrated and the residue crystallized from ethyl acetate (30 ml) at 4° C. for 2 days to yield 6.2 g of the same product. Yield of compound 3 was 45.7 g (34%), mp. 117-118° C.

3-Benzyl-9-methyl-3,9-diazabicyclo[3.3.1]nonane
(Intermediate compound 4)

To a solution of compound 3 (45.7 g, 0.177 mol) in 1,4-dioxane (400 ml) placed into a three-necked round bottom flask (1000 ml), LiAlH$_4$ (9.0 g, 0.237 mol) was added in small portions and the mixture was refluxed under argon for 18 hours. The reaction mixture was cooled to 80° C. and a mixture of water (9 ml) and 1,4-dioxane (40 ml) was dropped carefully into reaction flask (caution: vigorous hydrogen evolution). A fine suspension was cooled to room temperature and treated with KOH solution (20 g in 50 ml of water). The organic phase was decanted and concentrated under reduced pressure. The residue was distilled on Büchi oven in vacuo (0.1 mbar) at 130° C. The third collecting flask contained 3,9-diazabicyclo[3.3.1]nonane 4 (29.2 g, 72%) as a viscous colourless oil.

9-Methyl-3,9-diazabicyclo[3.3.1]nonane
(Intermediate compound 5)

To a solution of compound 4 (28.7 g, 0.125 mol) in absolute ethanol (100 ml) was added 10% Pd/C catalyst (6.3 g) under argon. The solution was hydrogenated with H$_2$ at 60 bar and 100° C. for 16 hours. The solution was filtered of on a Büchner funnel, the filtrate was concentrated under reduced pressure on a rotary evaporator and the residue distilled on Büchi oven in vacuo (0.1 mbar) at 100° C. to afford compound 5 (8.5 g, 49%) as a colorless gel.

Reference related to the preparation of intermediate compounds 1-5: *Il Farmaco* 55 (8) August 2000, Pages 553-562.

Method C 3-(6-Iodo-pyridazin-3-yl)-9-methyl-9-aza-bicyclo
[3.3.1]nonane free base (Intermediate compound;
JBP 18097-a)

A mixture of 9-methyl-3,9-diazabicyclo[3.3.1]nonane (4.0 g, 28.5 mmol), 3,6-diiodopyridazine (9.5 g, 28.5 mmol), diisopropylethylamine (7.4 g, 57.0 mmol) and dioxane (50 ml) was stirred at 75° C. for 4 days. Aqueous sodium hydroxide (75 ml, 1 M) was added, dioxane was evaporated and the mixture was extracted twice with dichloromethane (2×75 ml). Chromatography on silica gel with dichloromethane, 10% methanol and 1% aqueous ammonia as solvent gave the title compound. Yield 4.61 g (47%). Mp. 163-166° C.

Method D

9-Methyl-3-(6-phenylethynyl-pyridazin-3-yl)-9-aza-
bicyclo[3.3.1]nonane fumaric acid salt
(Compound D1)

3-(6-Iodo-pyridazin-3-yl)-9-methyl-9-aza-bicyclo[3.3.1] nonane (0.50 g, 1.45 mmol), phenylacetylene (0.30 g, 2.90 mmol), diisopropylethylamine (0.37 g, 2.90 mmol), CuI (28 mg, 0.14 mmol), palladacycle (27 mg, 0.029 mmol) and dioxane (20 ml) was stirred at reflux for 3 days. Aqueous sodium hydroxide (30 ml, 1 M) was added, dioxane was evaporated and the mixture was extracted twice with dichloromethane (2×30 ml). Chromatography on silica gel with dichloromethane, 10% methanol and 1% aqueous ammonia as solvent gave the title compound. Yield 0.38 g (82%). The corresponding salt was obtained by addition of a diethyl ether and methanol mixture (9:1) saturated with fumaric acid. Mp. 196-204° C.

N-{4-[6-(9-Methyl-9-aza-bicyclo[3.3.1]non-3-yl)-
pyridazin-3-ylethynyl]-phenyl}acetamide free base
(Compound D2)

Was prepared by Method D from N-(4-ethynyl-phenyl)-acetamide. Mp. 270-271° C.

3-[4-(1H-Indol-5-ylethynyl)-phenyl]-9-methyl-3,9-
diaza-bicyclo[3.3.1]nonane fumaric acid salt
(Compound D3)

Was prepared according to Method B from 5-ethynyl-1H-indole. Mp. 298° C.

5-Ethynyl-1H-indole (Intermediate compound)

A mixture of 4-(1H-indol-5-yl)-2-methyl-but-3-yn-2-ol (6.6 g, 33.1 mmol), sodiumhydride, 60% in mineral oil (0.13 g, 3.3 mmol) and anhydrous toluene (100 ml) was stirred for 5 hours at 110° C. The crude mixture was evaporated. Chromatography on silica gel with dichloromethane, 10% methanol and 1% aqueous ammonia as solvent gave the title compound. Yield 3.44 g (74%). Oil.

4-(1H-Indol-5-yl)-2-methyl-but-3-yn-2-ol (Intermediate compound)

A mixture of 5-iodoindole (25 g, 102.9 mmol), triphenylphosphine (2.70 g, 10.3 mmol), CuI (1.96 g, 10.3 mmol), potassium carbonate (35.5 g, 257.2 mmol), palladium (5 wt. % on calcium carbonate, poisoned with lead) (0.55 g, 5.14 mmol) and 1,2-dimethoxyethane (250 ml) was stirred at room temperature for 0.5 hour. 2-Methyl-3-butyn-2-ol (21.6 g, 257 mmol) was added and the mixture was stirred for 15 hours at 100° C. The crude mixture was filtered through silica gel and aqueous hydrochloric acid (250 ml, 2 M) was added and extracted with toluene. The organic phase was dried and evaporated. Chromatography on silica gel with dichloromethane, 10% methanol and 1% aqueous ammonia as solvent gave the title compound. Yield 6.7 g (33%). Mp. 119-123° C.

Method E

4-[4-(9-Methyl-3,9-diaza-bicyclo[3.3.1]non-3-yl)-phenylethynyl]-phenylamine free base (Compound E1)

A mixture of N-{4-[6-(9-methyl-9-aza-bicyclo[3.3.1]non-3-yl)-pyridazin-3-ylethynyl]-phenyl}-acetamide (0.42 g, 1.11 mmol), aqueous sodium hydroxide (10 ml, 4 M) and ethanol (10 ml, 96%) was stirred for 2 hours at reflux. The mixture was evaporated. Water (30 ml) was added and the mixture was extracted twice with dichloromethane (2×30 ml). Chromatography on silica gel with dichloromethane, 10% methanol and 1% aqueous ammonia as solvent gave the title compound. Yield 0.30 g (80%). Mp. 191° C.

4-[6-(8-Methyl-3,8-diaza-bicyclo[3.2.1]oct-3-yl)-pyridazin-3-ylethynyl]-phenylamine free base (Compound E2)

Was prepared according to Method E from N-{4-[6-(8-methyl-3,8-diaza-bicyclo[3.2.1]oct-3-yl)-pyridazin-3-ylethynyl]-phenyl}-acetamide. Mp. 204-210° C.

Method F

N-{4-[6-(8-Methyl-3,8-diaza-bicyclo[3.2.1]oct-3-yl)-pyridazin-3-ylethynyl]-phenyl}-benzamide free base (Compound F1)

To a stirred mixture of 4-[6-(8-methyl-3,8-diaza-bicyclo[3.2.1]oct-3-yl)-pyridazin-3-ylethynyl]-phenylamine (0.53 g, 1.66 mmol) and dichloromethane (20 ml) was added: benzoylchloride (0.35 g, 2.5 mmol) solved in dichloromethane (20 ml). The mixture was stirred at 0° C. for 2 hours and was then allowed to stir at room temperature for 15 hours. Aqueous sodium hydroxide (20 ml, 1 M) was added and the mixture was extracted with dichloromethane (3×30 ml). The mixture was dried and evaporated. Mp 88-96° C. LC-ESI-HRMS of [M+H]+ shows 424.2145 Da. Calc. 424.213735 Da, dev. 1.8 ppm.

N-{4-[6-(8-Methyl-3,8-diaza-bicyclo[3.2.1]oct-3-yl)-pyridazin-3-ylethynyl]-phenyl}-propionamide fumaric acid salt (Compound F2)

Was prepared according to Method F from 4-[6-(8-methyl-3,8-diaza-bicyclo[3.2.1]oct-3-yl)-pyridazin-3-ylethynyl]-phenylamine and propionic anhydride. Mp 238° C. LC-ESI-HRMS of [M+H]+ shows 376.2153 Da. Calc. 376.213735 Da, dev. 4.2 ppm.

N-{4-[6-(8-Methyl-3,8-diaza-bicyclo[3.2.1]oct-3-yl)-pyridazin-3-ylethynyl]-phenyl}-isobutyramide fumaric acid salt (Compound F3)

Was prepared according to Method F from 4-[6-(8-methyl-3,8-diaza-bicyclo[3.2.1]oct-3-yl)-pyridazin-3-ylethynyl]-phenylamine and isobutyric anhydride. Mp 214° C. LC-ESI-HRMS of [M+H]+ shows 390.231 Da. Calc. 390.229385 Da, dev. 4.1 ppm.

1-Ethyl-3-{4-[6-(8-methyl-3,8-diaza-bicyclo[3.2.1]oct-3-yl)-pyridazin-3-ylethynyl]-phenyl}-urea free base (Compound F4)

Was prepared according to Method F from 4-[6-(8-methyl-3,8-diaza-bicyclo[3.2.1]oct-3-yl)-pyridazin-3-ylethynyl]-phenylamine and ethylisocyanate. Mp 269° C. LC-ESI-HRMS of [M+H]+ shows 391.2253 Da. Calc. 391.224634 Da, dev. 1.7 ppm.

N-(4-Ethynyl-phenyl)-acetamide (Intermediate compound)

Was prepared according to Method F from 4-ethynyl-phenylamine.

8,8-Dimethyl-3-(6-phenylethynyl-pyridazin-3-yl)-3,8-diaza-bicyclo[3.2.1]octane onium iodide salt (Compound F5)

Iodomethane (0.23 g, 1.6 mmol) solved in dichloromethane (20 ml) was added to mixture of 8-methyl-3-(6-phenylethynyl-pyridazin-3-yl)-3,8-diaza-bicyclo[3.2.1]octane (0.50 g, 1.6 mmol) and dichloromethane (20 ml) at −70° C. The mixture was stirred at −70° C. for 1 hour. The mixture was allowed to reach room temperature and was stirred for 3 days. The mixture was evaporated and a mixture of methanol/ether (5%, 20 ml) was added, followed by filtration. The crystalline product was dried. LC-ESI-HRMS of M+ shows 319.1935 Da. Calc. 319.1923 Da, dev. 3.8 ppm.

Example 2

In Vitro Inhibition of $^3$H-α-Bungarotoxine Binding in Rat Brain

In this example the affinity of the compounds of the invention for binding to $\alpha_7$-subtype of nicotinic receptors is determined.

α-Bungarotoxine is a peptide isolated from the venom of the Elapidae snake *Bungarus multicinctus*. It has high affinity for neuronal and neuromuscular nicotinic receptors, where it acts as a potent antagonist. $^3$H-α-Bungarotoxine labels nicotinic acetylcholine receptors formed by the $\alpha_7$ subunit isoform found in brain and the $\alpha_1$ isoform in the neuromuscular junction.

Tissue Preparation

Preparations are performed at 0-4° C. Cerebral cortices from male Wistar rats (150-250 g) are homogenised for 10 seconds in 15 ml of 20 mM Hepes buffer containing 118 mM NaCl, 4.8 mM KCl, 1.2 mM $MgSO_4$ and 2.5 mM $CaCl_2$ (pH 7.5) using an Ultra-Turrax homogeniser. The tissue suspension is subjected to centrifugation at 27,000×g for 10 minutes. The supernatant is discarded and the pellet is washed twice by centrifugation at 27,000×g for 10 minutes in 20 ml of fresh buffer, and the final pellet is then re-suspended in fresh buffer containing 0.01% BSA (35 ml per g of original tissue) and used for binding assays.

Assay

Aliquots of 500 μl of homogenate are added to 25 μl of test solution and 25 μl of $^3$H-α-bungarotoxine (2 nM, final concentration) and mixed and incubated for 2 hours at 37° C. Non-specific binding is determined using (−)-nicotine (1 mM, final concentration). After incubation, the samples are added 5 ml of ice-cold Hepes buffer containing 0.05% PEI and poured directly onto Whatman GF/C glass fibre filters (pre-soaked in 0.1% PEI for at least 6 hours) under suction, and immediately washed with 2×5 ml ice-cold buffer.

The amount of radioactivity on the filters is determined by conventional liquid scintillation counting. Specific binding is total binding minus non-specific binding.

The test value is given as an $IC_{50}$ (the concentration of the test substance which inhibits the specific binding of $^3$H-α-bungarotoxin by 50%).

The results of these experiments are presented in Table 1 below.

TABLE 1

Inhibition of $^3$H-α-Bungarotoxine Binding

| Compound No. | $IC_{50}$ (μM) |
|---|---|
| B1 | 0.47 |

The invention claimed is:

1. A diazabicyclic aryl compound represented by Formula I any of its enantiomers or any mixture of its enantiomers, or a pharmaceutically acceptable salt thereof, wherein
m is 2 or 3; and
n is 1 or 2; and
$R^1$ represents hydrogen, alkyl, cycloalkyl or cycloalkyl-alkyl;
A represents a pyridazinylene group;
B represents a phenyl or naphthyl group, a 5-6 membered aromatic monocyclic heterocyclic group, or an aromatic bicyclic heterocyclic group; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, —NH(CO) R' and NH(CO)NHR'; wherein R' represents hydrogen, alkyl, cycloalkyl or phenyl; and
L represents —O—, —S—, —S—CH$_2$—, —CH$_2$—S—, —SO—, —SO$_2$—, —NR"—, —CH$_2$—, —CH$_2$—CH$_2$—, —CH═CH—, —C≡C—, —NR"CO—, —NR"CONR"— or —NR"(SO$_2$)—; wherein R" represents hydrogen or alkyl.

2. The diazabicyclic aryl compound of claim 1, or a pharmaceutically acceptable salt thereof, wherein
m is 2 or 3; and
n is 1 or 2.

3. The diazabicyclic aryl compound of claim 1, or a pharmaceutically acceptable salt thereof, wherein $R^1$ represents hydrogen, alkyl, cycloalkyl or cycloalkyl-alkyl.

4. The diazabicyclic aryl compound of claim 1, or a pharmaceutically acceptable salt thereof, wherein B represents a phenyl or naphthyl group, a 5-6 membered aromatic monocyclic heterocyclic group, or an aromatic bicyclic heterocyclic group; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, —NH(CO)R' and NH(CO)NHR'; wherein R' represents hydrogen, alkyl, cycloalkyl or phenyl.

5. The diazabicyclic aryl compound of claim 4, or a pharmaceutically acceptable salt thereof, wherein B represents phenyl, thiadiazolyl, pyridyl, pyridazinyl or indolyl; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, —NH(CO)R' and NH(CO)NHR'; wherein R' represents alkyl, cycloalkyl or phenyl.

6. The diazabicyclic aryl compound of claim 1, or a pharmaceutically acceptable salt thereof, wherein B represents an aromatic bicyclic heterocyclic group; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, —NH(CO)R' and NH(CO)NHR'; wherein R' represents alkyl, cycloalkyl or phenyl.

7. The diazabicyclic aryl compound of claim 1, or a pharmaceutically acceptable salt thereof, wherein
m is 2 or 3;
n is 1 or 2;
A represents ; and B represents phenyl, naphthyl, thiadiazolyl, pyridyl, pyridazinyl or indolyl; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, —NH(CO) R' and NH(CO)NHR'; wherein R' represents alkyl, cycloalkyl or phenyl.

8. The diazabicyclic aryl compound of claim 1, or a pharmaceutically acceptable salt thereof, wherein L represents —O—, —S—, —S—CH$_2$—, —CH$_2$—S—, —SO—, —SO$_2$—, —NR"—, —CH$_2$—, —CH$_2$—CH$_2$—, —CH═CH—, —C≡C—, —NR"CO—, —NR"CONR"— or —NR"(SO$_2$)—; wherein R" represents hydrogen or alkyl.

9. The diazabicyclic aryl compound of claim 8, or a pharmaceutically acceptable salt thereof, wherein L represents —O—, —S—, —S—CH$_2$—, —SO—, —C≡C—, —NHCO—, —NHCONH— or —NH(SO$_2$)—.

10. The diazabicyclic aryl compound of claim 1, or a pharmaceutically acceptable salt thereof wherein
    n is 1 or 2;
    A represents pyridazinyl;
    B represents a phenyl, pyridyl or indolyl, optionally substituted with substituents selected from the group consisting of alkyl, cycloalkyl, hydroxy, alkoxy, cyanoalkyl, halo, trihaloalkyl, trihaloalkoxy, cyano, amino, nitro, —NH(CO)R' and NH(CO)NHR'; wherein R' represents alkyl, cycloalkyl or phenyl; and
    L represents —O—, —S—, —S—CH$_2$—, —SO—, —C≡C—, —NHCO—, —NHCONH— or —NH(SO$_2$)—.

11. The diazabicyclic aryl compound of claim 7, or a pharmaceutically acceptable salt thereof, wherein
    m is 2 or 3;
    n is 1 or 2;
    A represents

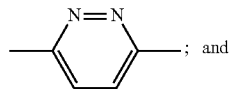
; and

B represents a phenyl, naphthyl, thiadiazolyl, pyridyl, pyridazinyl or indolyl; which aromatic group may optionally be substituted one or two times with substituents selected from the group consisting of alkyl, cycloalkyl, hydroxy, alkoxy, cyanoalkyl, halo, trihaloalkyl, trihaloalkoxy, amino, nitro, —NH(CO)R' and NH(CO)NHR'; wherein R' represents alkyl, cycloalkyl or phenyl.

12. The diazabicyclic aryl compound of claim 11, which is 8-Methyl-3-(6-phenylethynyl-pyridazin-3-yl)-3,8-diazabicyclo[3.2.1]octane;
(±)-9-Methyl-3-(6-phenylethynyl-pyridazin-3-yl)-3,9-diaza-bicyclo[4.2.1]nonane;
N-{4-[6-(9-Methyl-9-aza-bicyclo[3.3.1]non-3-yl)-pyridazin-3-ylethynyl]-phenyl}-acetamide;
9-Methyl-3-(6-phenylethynyl-pyridazin-3-yl)-9-aza-bicyclo[3.3.1]nonane;
4-[4-(9-Methyl-3,9-diaza-bicyclo[3.3.1]non-3-yl)-phenylethynyl]-phenylamine;
3-[4-(1H-Indol-5-ylethynyl)-phenyl]-9-methyl-3,9-diaza-bicyclo[3.3.1]nonane;
N-{4-[6-(8-Methyl-3,8-diaza-bicyclo[3.2.1]oct-3-yl)-pyridazin-3-ylethynyl]-phenyl}-acetamide;
4-[6-(8-Methyl-3,8-diaza-bicyclo[3.2.1]oct-3-yl)-pyridazin-3-ylethynyl]-phenylamine;
N-{4-[6-(8-Methyl-3,8-diaza-bicyclo[3.2.1]oct-3-yl)-pyridazin-3-ylethynyl]-phenyl}-benzamide;
N-{4-[6-(8-Methyl-3,8-diaza-bicyclo[3.2.1]oct-3-yl)-pyridazin-3-ylethynyl]-phenyl}-propionamide;
N-{4-[6-(8-Methyl-3,8-diaza-bicyclo[3.2.1]oct-3-yl)-pyridazin-3-ylethynyl]-phenyl}-isobutyramide;
3-[6-(1H-Indol-5-ylethynyl)-pyridazin-3-yl]-8-methyl-3,8-diaza-bicyclo[3.2.1]octane;
1-Ethyl-3-{4-[6-(8-methyl-3,8-diaza-bicyclo[3.2.1]oct-3-yl)-pyridazin-3-ylethynyl]-phenyl}-urea; or
8,8-Dimethyl-3-(6-phenylethynyl-pyridazin-3-yl)-3,8-diaza-bicyclo[3.2.1]octane onium iodide salt;
or an enantiomers or a mixture of its enantiomers, or a pharmaceutically acceptable salt thereof.

13. A pharmaceutical composition comprising a therapeutically effective amount of an diazabicyclic aryl compound of claim 1, or a pharmaceutically-acceptable addition salt thereof, or a prodrug thereof, together with at least one pharmaceutically-acceptable carrier or diluent.

14. The diazabicyclic aryl compound of claim 1, which is 8-Methyl-3-(6-phenylethynyl-pyridazin-3-yl)-3,8-diaza-bicyclo[3.2.1]octane; or enantiomers or a mixture of its enantiomers, or a pharmaceutically acceptable salt thereof.

* * * * *